United States Patent [19]

Kurihara et al.

[11] Patent Number: 5,153,003
[45] Date of Patent: Oct. 6, 1992

[54] COMPOSITION FOR FORMING ANTITHROMBOTIC MEDICAL APPLIANCES

[75] Inventors: Kozo Kurihara; Hironobu Saito; Yukie Misho; Takeshi Oshima, all of Tokyo, Japan

[73] Assignee: Sankyo Company Limited, Tokyo, Japan

[21] Appl. No.: 425,367

[22] Filed: Oct. 18, 1989

Related U.S. Application Data

[63] Continuation of Ser. No. 218,805, Jul. 13, 1988, abandoned.

[30] Foreign Application Priority Data

Jul. 14, 1987 [JP] Japan ................. 62-175236

[51] Int. Cl.⁵ ............. A61K 9/14; A61K 31/20; A01N 1/00
[52] U.S. Cl. .................... 424/487; 424/486; 424/422; 424/423; 514/560; 514/822; 514/953; 523/112; 523/113; 604/266
[58] Field of Search ............. 424/486, 487, 422, 423; 523/112, 113; 514/822, 950, 953, 560; 604/265, 266

[56] References Cited

U.S. PATENT DOCUMENTS

| | | | |
|---|---|---|---|
| 3,645,955 | 2/1972 | Flyn | 523/113 X |
| 3,767,695 | 10/1973 | Pike et al. | 514/822 X |
| 3,826,678 | 7/1974 | Hoffman et al. | 424/423 |
| 3,860,701 | 1/1975 | Short | 424/423 X |
| 3,932,656 | 1/1976 | Ramwell et al. | 424/423 |
| 4,360,685 | 11/1982 | Haslanger et al. | 514/822 X |
| 4,425,358 | 1/1984 | Szantay et al. | 514/822 X |
| 4,433,072 | 2/1984 | Pusineri et al. | 523/113 X |
| 4,563,485 | 1/1986 | Fox, Jr. et al. | 523/113 |
| 4,604,412 | 8/1986 | Joh et al. | 523/112 |
| 4,713,402 | 12/1987 | Solomon | 523/112 |

FOREIGN PATENT DOCUMENTS

| | | |
|---|---|---|
| 136916 | 4/1985 | European Pat. Off. |
| 2821737 | 11/1978 | Fed. Rep. of Germany ...... 514/822 |
| 58-010539 | 7/1983 | Japan ................. 514/822 |
| 2012265 | 7/1979 | United Kingdom . |

OTHER PUBLICATIONS

Plastics in Medicine and Surgery, III, No. 31, 1979, pp. 31.1–31.7; J. C. McRea et al, "Prostaglandin releasing polymers for nonthrombogenic surfaces".

Primary Examiner—Thurman K. Page
Assistant Examiner—G. S. Kishore
Attorney, Agent, or Firm—Frishauf, Holtz, Goodman & Woodward

[57] ABSTRACT

A composition comprising a polymer having dispersed therethrough a prostacyclin derivative selected from the group consisting of compounds of formula (I):

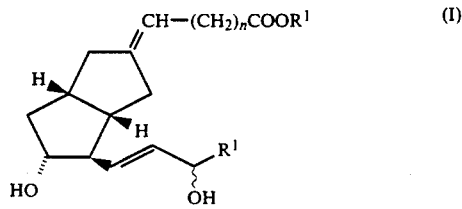

(in which $R^1$ represents hydrogen or lower alkyl, $R^2$ represents a $C_3$–$C_{12}$ alkyl group or a $C_3$–$C_{12}$ alkenyl group; and n is an integer from 1 to 5; and pharmaceutically acceptable salts thereof) can be used to make a medical appliance from which the prostaglandin, having antithrombotic properties, will be released gradually and in a controlled way.

8 Claims, No Drawings

COMPOSITION FOR FORMING ANTITHROMBOTIC MEDICAL APPLIANCES

This application is a continuation of application Ser. No. 07/218,805, filed Jul. 13, 1988, abandoned.

BACKGROUND TO THE INVENTION

The present invention relates to a polymeric composition containing certain specific antithrombotic prostacyclin derivatives and which has antithrombotic properties, enabling it to be used for the production of various medical appliances, notably appliances which are designed to come into contact with live blood.

Many medical prostheses and other medical appliances are made of plastics materials and are, but for one problem, in general extremely successful. The problem is that most such medical appliances provoke the formation of thrombi when they come into contact with blood and this, of course, is extremely dangerous. It is, therefore, essential that such thrombi should be prevented from forming.

In general terms, there are three ways in which the thrombi provoked by medical appliances can be prevented from forming:

(1) An antithrombotic agent may be added to the blood of the patient to alter the properties of the blood and reduce its ability to form thrombi;

(2) The structure of the medical appliances themselves may be made antithrombotic;

(3) The medical appliances may be made antithrombotic by incorporating into them one or more suitable antithrombotic drugs.

Of these, method (1) is often employed in practice, administering heparin or ticlopidine as the antithrombotic agent. This is, however, systemic, rather than local, application of the drug and the patient is subjected in full measure to any side effects or disadvantages of the antithrombotic drug in question. Also, of course, the antithrombotic effect is manifested in parts of the patient's body remote from the medical appliance and the normal advantageous effects of thrombi in inhibiting hemorrhaging are also prevented. In the case of ticlopidine, in particular, it takes more than a week after administration before the blood returns to its original condition in which thrombi can form when required, and the hemorrhaging which can occur during this period can give rise to serious problems.

Method (2) involves the design of the medical appliance in such a way as to minimize any physical loci which can act as foci for the development of thrombi. Although experimental work involving the relationships between structures comprising several microphases or specific fluctuations of the surface structure and antithrombotic properties has been carried out in an attempt to employ method (2), satisfactory results have not been obtained to date and thus this method cannot be used in practice to provide an antithrombotic medical appliance.

Method (3) is superior both theoretically and also having regard to present technological abilities to both methods (1) and (2). Unfortunately, prior to the present invention, although certain medical appliances incorporating antithrombotic drugs have been made commercially, it is apparent, even on theoretical grounds, that the products so far produced commercially cannot be totally satisfactory, as explained below. Moreover, although the products are undoubtedly far better than are corresponding medical appliances which do not incorporate the antithrombotic drugs, as can be seen below, these appliances are still far from satisfactory.

Principally, three classes of drugs have been investigated with a view to incorporating them into medical appliances. These are heparin, urokinase and certain prostaglandins (notably $PGE_1$). Medical appliances made of polyvinyl chloride incorporating either heparin or urokinase are currently available and have been used in practice.

The formation of endogenous thrombi is caused predominantly either by the coagulation factor system or by the platelet system. Heparin, on the one hand, seems to suppress the activity of the coagulation factor system but does not suppress the platelet system. As a result, the formation of thrombi by the platelet system cannot be prevented by heparin. Moreover, when a platelet system thrombus forms, anti-heparin factor is released from the thrombus, subsequently reducing the effect of the heparin. Accordingly, heparin alone has a very limited ability to prevent thrombosis. On the other hand, the activity of urokinase is to convert plasminogen to plasmin, a proteolytic enzyme which has fibrinolytic effects, and thus its effect, indirectly, is to dissolve thrombi which have already formed, but it cannot prevent the growth or formation of such thrombi. Thus, although it can have some beneficial effects on patients by gradually causing the removal of a thrombus and thereby alleviating any disorders resulting therefrom, it cannot prevent the formation of thrombi and the resulting disorders.

Attempts have also been made to use certain prostaglandins as the antithrombotic drug to be incorporated into the plastics material. For example, as described by H. Jacobs et al ["$PGE_1$—Heparin Conjugate Releasing Polymers", Journal of Controlled Release, 2, 313 (1985)], attempts have been made to use $PGE_1$ in certain polymers, and, although a controlled release of the drug was achieved, fibrin and other cells still adhered to the surface, thus rendering this product unsatisfactory. When attempts were then made to overcome this problem by using a combination of heparin with the prostaglandin, the $PGE_1$ bioactivity was reduced. Another problem that has deterred experimenters from using prostaglandin derivatives is their instability, which leads them to degrade and thus lose activity when incorporated into plastics materials.

In all of the above methods, where an active compound is incorporated in a polymer, this has been achieved by forming a coating of the active compound on the surface of the polymer, specifically, on the surface of the medical appliance formed therefrom.

There has also been a reported attempt to overcome this problem by grafting an ester of the platelet aggregation inhibitor, 5-(6-carboxyhexyl)-1-(3-cyclohexyl-3-hydroxypropyl)hydantoin, with a vinylic monomer, e.g. 2-hydroxyethyl methacrylate, onto a poly(etherurethane) (Biomer) [see Chemical Abstracts, 101, (1984), 101:216336r].

We have now surprisingly found that certain prostacyclin derivatives can be incorporated into plastics materials and will maintain essentially the whole of their activity, indicating that there is little or no degradation, and will moreover be released gradually into the bloodstream when used in or in association with the living body. Unlike the majority of the prior art, in the present invention, the active compounds are dispersed throughout a polymer, which is used as or as part of a medical appliance.

BRIEF SUMMARY OF INVENTION

Thus, in its broadest aspect, the present invention consists in an antithrombotic composition comprising a medically acceptable polymer having distributed therethrough at least one prostacyclin selected from the group consisting of compounds of formula (I):

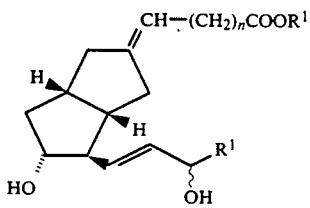

in which:
$R^1$ represents a hydrogen atom or a $C_1$–$C_6$ alkyl group;
$R^2$ represents a $C_3$–$C_{12}$ alkyl group or a $C_3$–$C_{12}$ alkenyl group; and
n is an integer of from 1 to 5;
and pharmaceutically acceptable salts thereof.

The invention also provides a medical appliance wherein at least a surface portion thereof is composed of a polymer composition according to the present invention, especially, but not exclusively, a catheter.

DETAILED DESCRIPTION OF INVENTION

In the compounds of formula (I), $R^1$ represents a hydrogen atom (i.e. the compound is the free acid) or a $C_1$–$C_6$ alkyl group, which may be a straight or branched chain group, and is preferably a group containing from 1 to 5 carbon atoms, for example a methyl, ethyl, propyl, isopropyl, butyl, isobutyl, pentyl or isopentyl group (i.e. the compound is an alkyl ester of one of the above acids).

$R^2$ may represent an alkyl group containing from 3 to 12 carbon atoms, which may be a straight or branched chain alkyl group, for example a propyl, isopropyl, butyl, isobutyl, pentyl, isopentyl, 1-methylpentyl, 2-methylpentyl, hexyl, hepthyl, 1,1-dimethylpentyl, 2-ethylpentyl, octyl, 2-methyloctyl, nonyl, 2-methylnonyl, 2-ethyloctyl, decyl, 2-methyldecyl or 2-ethyldecyl group. Alternatively, it may represent an alkenyl group containing from 3 to 12 carbon atoms, which may be a straight or branched chain alkenyl group, for example an allyl, 2-butenyl, 3-pentenyl, 2-methyl-3-pentenyl, 4-hexenyl, 5-heptenyl, 6-methyl-5-heptenyl, 2,6-dimethyl-5-heptenyl, 1,1,6-trimethyl-5-heptenyl, 6-methyl-5-octenyl, 2,6-dimethyl-5-octenyl, 6-ethyl-5-octenyl, 2-methyl-6-ethyl-5-octenyl or 2,6-diethyl-5-octenyl group.

The number of methylene groups in the side chain, represented by "n", may be any integer from 1 to 5, but is preferably from 2 to 4, and is more preferably 3.

In particular, preferred compounds of the present invention are those compounds of formula (I) in which:
$R^1$ represents a hydrogen atom or an alkyl group having from 1 to 3 carbon atoms, such as a methyl, ethyl, propyl or isopropyl group;
$R^2$ represents an alkyl group having from 4 to 10 carbon atoms, such as a butyl, isobutyl, pentyl, isopentyl, 1-methylpentyl, 2-methylpentyl, hexyl, isoheptyl, 1,1-dimethylpentyl, 2-ethylpentyl, octyl, 2-methyloctyl or 2-ethyloctyl group, or an alkenyl group having from 5 to 12 carbon atoms, such as a 3-pentenyl, 2-methyl-3-pentenyl, 4-hexenyl, 5-heptenyl, 6-methyl-5-heptenyl, 2,6-dimethyl-5-heptenyl, 1,1,6-trimethyl-5-heptenyl, 6-methyl-5-octenyl, 2,6-dimethyl-5-octenyl, 6-ethyl-5-octenyl, 2-methyl-6-ethyl-5-octenyl or 2,6-diethyl-5-octenyl group; and
preferably n is 3.

Of the compounds of formula (I), any compound where $R^1$ represents a hydrogen atom may be converted to a corresponding pharmaceutically acceptable salt, if desired. Examples of suitable pharmaceutically acceptable salts include: salts with an alkali metal or an alkaline earth metal, such as the sodium, potassium, magnesium or calcium salts; the ammonium salt; quaternary ammonium salts, such as the tetramethylammonium, tetraethylammonium, benzyltrimethylammonium or phenyltriethylammonium salts; salts with lower aliphatic, lower alicyclic or lower arylaliphatic amines, such as the methylamine, ethylamine, dimethylamine, diethylamine, trimethylamine, triethylamine, N-methylhexylamine, cyclopentylamine, dicyclohexylamine, benzylamine, dibenzylamine, α-phenylethylamine or ethylenediamine salts; salts with heterocyclic amines and lower alkyl derivatives thereof, such as the piperidine, morpholine, pyrrolidine, piperazine, pyridine, 1-methylpiperazine or 4-ethylmorpholine salts; salts with amines having hydrophilic groups, such as the monoethanolamine, ethyldiethanolamine or 2-amino-1-butanol salts; and salts with 1-threo-2-amino-3-p-nitrophenyl-1,3-propanediol.

The compounds of formula (I) can exist as various stereoisomeric forms due to the configuration of the hydroxyl group of the side chain on the cyclopentane ring, the double bond between the adjacent carbon atoms of the side chain and the cyclopentane ring and, where $R^2$ represents an alkenyl group, the double bond between the carbon atoms in the alkenyl group of the compound. The individual isomers may be prepared by stereo-specific synthesis techniques, as are well known in the art, or a mixture of isomers may be prepared and then, if desired, separated by well known resolution techniques. Alternatively, the compounds may be employed as mixtures of two or more such isomers. It is well known that pharmacologically active compounds often exhibit greater activity in the form of specific isomers, and, if desired, simple experimentation will reveal which, if any, of the isomers of the compounds of formula (I) is the more active. Although both stereoisomers and mixtures of the stereoisomers are indicated above by a single formula, the present invention envisages the use of either the individual, isolated isomers or of mixtures of any two or more such isomers, whether obtained by non-stereospecific synthesis, mixing or otherwise.

Particularly preferred compounds of formula (I) include:
6,9-methylene-11,15-dihydroxyprost-5,13-dienoic acid;
6,9-methylene-11,15-dihydroxy-17-methylprost-5,13-dienoic acid;
6,9-methylene-11,15-dihydroxy-16,16-dimethylprost-5,13-dienoic acid;
6,9-methylene-11,15-dihydroxy-20-isopropylideneprost-5,13-dienoic acid; and
6,9-methylene-11,15-dihydroxy-17-methyl-20-isopropylideneprost-5,13-dienoic acid {otherwise known as 7-(4-carboxybutylidene)-3-hydroxy-2-(3-hydroxy-5,9-dimethyl-1,8-decadienyl)-[3.3.0]-bicyclooctane};

and pharmaceutically acceptable salts thereof.

In particular, we prefer the following isomers of the above compounds:

6,9α-methylene-11α,15α-dihydroxyprost-5(Z),13(E)-dienoic acid;
6,9α-methylene-11α,15β-dihydroxyprost-5(Z),13(E)-dienoic acid;
6,9α-methylene-11α,15α-dihydroxyprost-5(E),13(E)-dienoic acid;
6,9α-methylene-11α,15β-dihydroxyprost-5(E),13(E)-dienoic acid;
6,9α-methylene-11α,15α-dihydroxy-17-methylprost-5(Z),13(E)-dienoic acid;
6,9α-methylene-11α,15β-dihydroxy-17-methylprost-5(Z),13(E)-dienoic acid;
6,9α-methylene-11α,15α-dihydroxy-17-methylprost-5(E),13(E)-dienoic acid;
6,9α-methylene-11α,15β-dihydroxy-17-methylprost-5(E),13(E)-dienoic acid;
6,9α-methylene-11α,15α-dihydroxy-16,16-dimethyl-prost-5(Z),13(E)-dienoic acid;
6,9α-methylene-11α,15β-dihydroxy-16,16-dimethyl-prost-5(Z),13(E)-dienoic acid;
6,9α-methylene-11α,15α-dihydroxy-16,16-dimethyl-prost-5(E),13(E)-dienoic acid;
6,9α-methylene-11α,15β-dihydroxy-16,16-dimethyl-prost-5(E),13(E)-dienoic acid;
6,9α-methylene-11α,15α-dihydroxy-20-isopropylidene-prost-5(Z),13(E)-dienoic acid;
6,9α-methylene-11α,15β-dihydroxy-20-isopropylidene-prost-5(Z),13(E)-dienoic acid;
6,9α-methylene-11α,15α-dihydroxy-20-isopropylidene-prost-5(E),13(E)-dienoic acid;
6,9α-methylene-11α,15β-dihydroxy-20-isopropylidene-prost-5(E),13(E)-dienoic acid;
6,9α-methylene-11α,15α-dihydroxy-17-methyl-20-isopropylideneprost-5(Z),13(E)-dienoic acid;
6,9α-methylene-11α,15β-dihydroxy-17-methyl-20-isopropylideneprost-5(Z),13(E)-dienoic acid;
6,9α-methylene-11α,15α-dihydroxy-17-methyl-20-isopropylideneprost-5(E),13(E)-dienoic acid {otherwise known as (1S, 2S, 3R, 5S, 7E)-7-(4-carboxybutylidene)-3-hydroxy-2-[(1E, 3S, 5R)-3-hydroxy-5,9-dimethyl-1,8-decadienyl]-[3.3.0]-bicyclooctane}; and
6,9α-methylene-11α,15β-dihydroxy-17-methyl-20-isopropylideneprost-5(E),13(E)-dienoic acid;

and pharmaceutically acceptable salts thereof.

The most preferred of these compounds is 6,9α-methylene-11α,15α-dihydroxy-17-methyl-20-isopropylideneprost-5(E),13(E)-dienoic acid and pharmaceutically acceptable salts thereof, the free acid itself being hereinafter referred to as "Compound A".

The compounds of formula (I) are all known compounds which may be prepared by known methods. They are described, inter alia, in United Kingdom Patent No. 2 012 265 and in U.S. patent application Ser. No. 840 920, filed Mar. 18, 1986, the disclosures of both on which are incorporated herein by reference.

The nature of the polymer used in the compositions and medical appliances of the present invention should be carefully chosen in the light of their intended use, as is well known in the art. Of the many polymers available for medical use, we have surprisingly found that the following give the best results in terms of the ability of the prostacyclin derivative to dissolve, disperse or diffuse itself in them: cellulose, cellulose acetate, chitin, chitosan, gelatine, collagen, atelocollagen, fibrin, alginic acid or a salt thereof, a polyhydroxyethyl methacrylate, a poly(ether-urethane-urea), a poly(ether-urethane), a silicone, a poly(amino acid), and copolymers of any two or more of the monomers forming said polymers. The more preferred of these polymers are: cellulose acetate, a poly(ether-urethane-urea), a poly(ether-urethane) and a silicone, of which the poly(ether-urethane-urea)s, cellulose acetates and silicones are most preferred, the silicones being the best of these.

The compounds of formula (I) may be incorporated into the polymer as such, or they may first be adsorbed on a suitable carrier, for example a cyclodextrin, another sugar or light anhydrous silicic anhydride. In order to enhance the antithrombotic activity, the compound of formula (I) may also, if desired, be used in combination with an anticoagulant, such as heparin or any of the other similarly active compounds referred to above in connection with the prior art.

There is no particular restriction on the way in which the prostacyclin derivative is incorporated into the polymer, provided that the effect is to disperse the prostacyclin, preferably essentially homogeneously, throughout the polymer. For example, a polymer compound may be soaked in a solution of the prostacyclin derivative, before of after forming the polymer compound into the shape of the desired medical appliance; the polymer may be compounded with the prostacyclin derivative, and, if desired, with any other conventional compounding ingredients, separately or together; the prostacyclin derivative may be incorporated into the polymer at the time of polymerization or of cross-linking; or a medical appliance may be coated with a polymer composition containing the prostacyclin derivative, and which may itself have been prepared by any of the above methods.

In view of the last of the methods suggested above, it will be understood that it is not necessary that the prostacyclin derivative be dispersed through the whole of the medical appliance, provided that it is dispersed throughout a polymer in at least a surface layer of the appliance. However, if desired, the whole of the medical appliance may be made of the composition of the invention.

There is no restriction on the concentration of the prostacyclin derivative of formula (I) in the polymer or compounded polymeric material from which the medical appliance is made, and some beneficial effect will be observed even at very low concentrations, for example 1 μg/ml. The optimum amount will depend on the migration or diffusion rate of the prostacyclin derivative in the polymer, which may be determined by simple routine experimentation, and also on the desired duration of the antithrombotic effect, as a higher concentration will tend to lead to a longer lasting effect. Although, therefore, a critical limit is difficult to define with any general exactitude, we would normally consider that a concentration of the prostacyclin in the polymer of at least 100 μg/ml is best, taking into account the desired duration of the antithrombotic activity. For the same reasons, the optimum upper limit is also difficult to define exactly and generally, but we consider that there would be no benefit to increasing the concentration beyond 750 mg/ml and there may be disadvantages, for example loss of mechanical strength.

Thus, although the range of concentrations of prostacyclin derivative in the polymer will normally be from 1 μg/ml to 750 mg/ml, amounts outside this range might be used in particular circumstances. However, the more preferred range of concentrations is from 50 μg/ml to 500 mg/ml, and the most preferred range is from 100 μg/ml to 100 mg/ml.

The resulting polymeric composition may be used to prepare any medical appliance, although, of course, the benefits of the present invention are only manifest when the appliance is to come into contact with live blood. Examples of medical appliances to which the composition of the invention may be applied include: blood bags, whether for use in vitro or otherwise; and artificial organs, artificial blood vessels and catheters, whether for use in vivo or in extracorporeal circulation systems (e.g. blood dialytic and artificial cardiopulmonary apparatus); and plasmapheretic apparatus; and there is, in general, no particular limitation to its use.

The invention is further illustrated by the following non-limiting Examples, in which all parts are parts by weight.

EXAMPLE 1

A silicone sheet (Silastic, medical grade, a trade mark for a product of Dow Corning K. K., Japan, 270 μm thick) was impregnated with an aqueous solution (pH 6–7) with a variety of concentrations of Compound A ranging from 0.1 to 100 μg/ml for two days to give silicone samples containing various amounts of Compound A. After impregnation, the sheet was wiped with a clean paper and was then air-dried. The silicone sheet was then cut to prepare samples each having a width of 0.8 mm and a length of 6 cm. The concentration of Compound A in the silicone rubber was measured by extracting the compound with chloroform, evaporating the solution to dryness, dissolving the residue in a phosphate buffer solution (pH 7.4) and then subjecting the resulting solution to high pressure liquid chromatography. The concentrations found are reported in the Table in Test Example 1.

EXAMPLE 2

10 g of Compound A and 40 g of light anhydrous silicic anhydride (Japanese Pharmacopoeia) were placed in a mortar. 32 g of distilled water were added to the mixture, which was then kneaded. The kneaded mixture was dried at 60° C. for 1 hour in an aerated dryer. At the end of this time, 10 g of the light anhydrous silicic anhydride on which the Compound A was adsorbed and 90 g of MDX 4-4210 (a trade name for a silicone rubber produced by Dow Corning K. K., Japan) were kneaded together using a roller with three rolls. After this 10 g of polymethylhydrogen siloxane (a cross-linking agent) were added. After mixing, the mixture was moulded and allowed to cross-link. In the course of this procedure, Compound A was observed to be dispersed in a stable state in the silicone with little, if any, decomposition as a result of the cross-linking.

EXAMPLE 3

6 g of Compound A and 40 g of light silicic anhydride were placed in a mortar. 32 g of distilled water were added to the mixture, which was then kneaded. The kneaded mixture was dried in an aerated dryer at 60° C. for 1 hour. At the end of this time, 16.5 g of this light silicic anhydride having absorbed therein the Compound A was dispersed into 24.5 g of silicone oil Fluid 360 (produced by Dow Corning K. K., Japan). The resulting dispersion was added to 784 g of a silicone rubber containing a crosslinking agent, and the resulting mixture was then kneaded with a twin roll kneader to effect dispersion. The resulting dispersion was subjected to extrusion molding by a conventional technique to form a catheter tube with an outer diameter of 1.7 mm and an inner diameter of 0.8 mm, and the tube was heat-treated at 120° C. for 1.5 minutes, after which it was subjected to ethylene oxide gas sterilization at 55° C. for 24 hours, and further deaeration at 55° C. over a day.

It was confirmed that the Compound A did not undergo any substantial decomposition and was dispersed in the silicone in a stable state.

EXAMPLE 4

A soft polyvinyl chloride tube with an outer diameter of 1.6 mm was coated over its outer surface as described below.

To a 15% w/w solution of a poly(ether-urethane-urea) (prepared from 4,4'-diphenylmethane diisocyanate, polytetramethylene glycol and ethylene diamine) in dimethylacetamide was added Compound A in an amount of 30 parts per 100 parts of the solution. The polyvinyl chloride tube described above was dipped into the resulting solution and was then dried at 70°–80° C. for 40–60 minutes. This dipping and drying step was repeated several times to form a coating layer with a thickness of about 250 μm over the tube. The resulting tube was then dried at 120° C. for 30 minutes, after which it was sterilized with ethylene oxide gas as described in Example 3. There was thus prepared a polyvinyl chloride tube having an outer surface layer in which Compound A was uniformly dispersed.

EXAMPLE 5

0.002 part of Compound A was dissolved in a solution of 5 parts of cellulose acetate LL-10 (available from Daicel Chemical Industries, Ltd.), 40 parts of dioxane, 40 parts of acrylonitrile and 15 parts of water, and the resulting solution was cast on a glass plate. The cast plate was dried at 40° C. for 20 hours to prepare a cast film.

In this example, it was confirmed that Compound A underwent hardly any decomposition and that it was dispersed in the cellulose acetate in a stable state.

TEST EXAMPLE 1

Male Wistar-Imamichi rats each weighing about 350 g were used in this test and each experiment was carried out on a group consisting of 6 animals. The carotid artery and the cervical vein in each rat were connected with a cannule under anesthesia by intraperitoneal injection of sodium thiobutabarbital at 100 mg/kg to form a A-V (arterial-venous) shunt. The cannule was a medical silicone tube having a silicone sheet in the middle thereof. The silicone sheet was in each case one of the samples prepared as described in Example 1.

After 15 minutes from the time when the blood began to flow, the cannule was removed and rinsed with a 3.8% w/v aqueous solution of sodium citrate. The silicone sheet was then removed, swept with a filter paper to remove water and weighed.

The weight of thrombi was determined by substracting the weight of the silicone sheet before testing from the weight of the silicone sheet after testing.

The results are summarized in the following Table:

TABLE

| Concentration of Compound A (μg/g) | Average weight of thrombus (mg) | Standard deviation (mg) |
| --- | --- | --- |
| 0 | 35.5 | 5.5 |
| 4.6 | 29.5 | 1.3 |
| 12 | 29.2 | 4.5 |
| 32.1 | 30.9 | 3.1 |
| 69 | 17.1 | 6.1 |
| 145 | 16.7 | 5.3 |
| 218 | 10.4 | 5.9 |
| 319 | 9.9 | 6.9 |
| 584 | 2.1 | 0.7 |

The excellent anti-thrombotic properties of the present medical appliance will be apparent from the above results.

In analyzing the above results, when the concentration of Compound A was 32.1 μg/g or less, an anti-thrombotic effect could not be observed. On the other hand, when the concentration of Compound A was more than 32.1 μg/g, an excellent anti-thrombotic effect could be observed and the relationship between the logarithm of the value of the concentration of Compound A and the weight of the thrombus was confirmed to be linear. A significant difference could be observed at a concentration of Compound A of not less than 50 μg/g as compared with the control not containing Compound A, by utilizing the said relationship.

TEST EXAMPLE 2

The catheter prepared as described in Example 3 was tested for its anti-thrombotic properties as follows:

Mongrel adult dogs, each group consisting of 5 animals, were used in this test.

The left internal jugular vein of each dog was exposed under general anesthesia and a residual catheter with a length of about 15 cm was kept within the vein toward the superior vena cava. After 4 weeks, the dog was killed, its chest was opened and the blood vessel was excised to take out the residual catheter. Then, thrombosis in the vessel and in the catheter was visually observed as compared with non-medicated control catheters. Hardly any thrombosis was observed in both the blood vessel and the catheter prepared by Example 3.

We claim:

1. A medical appliance wherein at least a surface portion thereof is composed of an antithrombotic composition comprising a medically acceptable polymer having distributed therethrough an antithrombotic effective amount of a prostacyclin or mixture prostacyclins selected from the group consisting of compounds of formula (I):

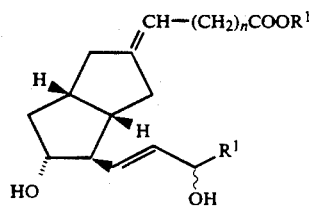

in which:

$R^1$ represents a hydrogen atom or a $C_1$-$C_6$ alkyl group;

$R^2$ represents a $C_3$-$C_{12}$ alkyl group or a $C_3$-$C_{12}$ alkenyl group; and n is an integer of from 1 to 5;

and pharmaceutically acceptable salts thereof, and wherein said polymer is silicone.

2. A medical appliance as claimed in claim 1, wherein:
$R^1$ represents a hydrogen atom or a $C_1$-$C_5$ alkyl group; and
$R^2$ represents a $C_4$-$C_{10}$ alkyl group or a $C_5$-$C_{12}$ alkenyl group.

3. A medical appliance as claimed in claim 1, wherein:
$R^1$ represents a hydrogen atom or a $C_1$-$C_3$ alkyl group; and
$R^2$ represents a $C_4$-$C_{10}$ alkyl group or a $C_5$-$C_{12}$ alkenyl group.

4. A medical appliance as claimed in claim 1, wherein n is 3.

5. A medical appliance as claimed in claim 1, wherein said prostacyclin is selected from the group consisting of:

6,9-methylene-11,15-dihydroxyprost-5,13-dienoic acid;

6,9-methylene-11,15-dihydroxy-17-methylprost-5,13-dienoic acid;

6,9-methylene-11,15-dihydroxy-16,16-dimethylprost-5,13-dienoic acid;

6,9-methylene-11,15-dihydroxy-20-isopropylideneprost-5,13-dienoic acid;

6,9-methylene-11,15-dihydroxy-17-methyl-20-isopropylideneprost-5,13-dienoic acid; and and pharmaceutically acceptable salts thereof.

6. A medical appliance as claimed in claim 1, wherein said prostacyclin is selected from the group consisting of:

6,9α-methylene-11α,15α-dihydroxyprost-5(Z),13(E)-dienoic acid;

6,9α-methylene-11α,15β-dihydroxyprost-5(Z),13(E)-dienoic acid;

6,9α-methylene-11α,15α-dihydroxyprost-5(E),13(E)-dienoic acid;

6,9α-methylene-11α,15β-dihydroxyprost-5(E),13(E)-dienoic acid;

6,9α-methylene-11α,15α-dihydroxy-17-methylprost-5(Z),13(E)-dienoic acid;

6,9α-methylene-11α,15β-dihydroxy-17-methylprost-5(Z),13(E)-dienoic acid;

6,9α-methylene-11α,15α-dihydroxy-17-methylprost-5(E),13(E)-dienoic acid;

6,9α-methylene-11α,15β-dihydroxy-17-methylprost-5(E),13(E)-dienoic acid;

6,9α-methylene-11α,15α-dihydroxy-16,16-dimethylprost-5(Z),13(E)-dienoic acid;

6,9α-methylene-11α,15β-dihydroxy-16,16-dimethylprost-5(Z),13(E)-dienoic acid;

6,9α-methylene-11α,15α-dihydroxy-16,16-dimethylprost-5(E),13(E)-dienoic acid;

6,9α-methylene-11α,15β-dihydroxy-16,16-dimethylprost-5(E),13(E)-dienoic acid;

6,9α-methylene-11α,15α-dihydroxy-20-isopropylideneprost-5(Z),13(E)-dienoic acid;

6,9α-methylene-11α,15β-dihydroxy-20-isopropylideneprost-5(Z),13(E)-dienoic acid;

6,9α-methylene-11α,15α-dihydroxy-20-isopropylideneprost-5(E),13(E)-dienoic acid;

6,9α-methylene-11α,15β-dihydroxy-20-isopropylideneprost-5(E),13(E)-dienoic acid;

6,9α-methylene-11α,15α-dihydroxy-17-methyl-20-isopropylideneprost-5(Z),13(E)-dienoic acid;

6,9α-methylene-11α,15β-dihydroxy-17-methyl-20-isopropylideneprost-5(Z),13(E)-dienoic acid;

6,9α-methylene-11α,15α-dihydroxy-17-methyl-20-isopropylideneprost-5(E),13(E)-dienoic acid and;

6,9α-methylene-11α,15β-dihydroxy-17-methyl-20-isopropylideneprost-5(E),13(E)-dienoic acid;

and pharmaceutically acceptable salts thereof.

7. A medical appliance as claimed in claim 1, which is a catheter.

8. A medical appliance as claimed in claim 6, which is a catheter.

* * * * *